United States Patent [19]
Casara et al.

[11] 4,088,667
[45] May 9, 1978

[54] LOWER ALKYL 2-TRI-(LOWER)ALKYLSILYLACETYLENE-N-CARBETHOXYGLYCINATES AND PROCESS FOR USING SAME

[75] Inventors: Patrick J. Casara, Strasbourg; Michel Jung, Illkirch Graffenstaden; Brian Walter Metcalf, Strasbourg, all of France

[73] Assignee: Merrell Toraude et Compagnie, Strasbourg, France

[21] Appl. No.: 812,065

[22] Filed: Jul. 1, 1977

[51] Int. Cl.² .............................................. C07F 7/10
[52] U.S. Cl. ...................... 260/448.2 N; 260/448.2 E; 424/184
[58] Field of Search ................................ 260/448.2 N

[56] References Cited

U.S. PATENT DOCUMENTS 3,946,060   3/1976   Metcalf et al. ............... 260/448.2 N Primary Examiner—Paul F. Shaver
Attorney, Agent, or Firm—L. Ruth Hattan; Eugene O. Retter; George W. Rauchfuss, Jr.

[57] ABSTRACT

Novel compounds of the formula

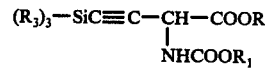

wherein each of R and $R_1$ is a lower alkyl group of from 1 to 4 carbon atoms, $R_3$ is an alkyl group and a process employing said compounds.

3 Claims, No Drawings

LOWER ALKYL 2-TRI-(LOWER)ALKYLSILYLACETYLENE-N-CARBETHOXYGLYCINATES AND PROCESS FOR USING SAME

FIELD OF INVENTION

This invention relates to novel compounds which are useful as starting materials for the preparation of pharmacologically useful compounds or of compounds which are intermediates in the preparation of pharmacologically useful compounds and a process employing said starting materials.

SUMMARY OF INVENTION

The novel compounds of the present invention are represented by the following general Formula I:

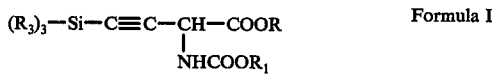

Formula I wherein each of R and $R_1$ is a straight chain lower alkyl group of from 1 to 4 carbon atoms, specifically methyl, ethyl, n-propyl and n-butyl and can be the same or different, and $R_3$ is methyl, ethyl, n-propyl or n-butyl and each $R_3$ is the same or two $R_3$ groups are methyl and the other $R_3$ group is tert-butyl.

The compounds of general Formula I are useful as antibacterial agents and as starting materials for the preparation of pharmacologically useful agents or for the preparation of compounds which are useful as intermediates in the preparation of pharmacologically useful agents.

This invention also relates to a novel process employing the compounds of general Formula I.

DETAILED DESCRIPTION OF INVENTION

Illustrative examples of the compounds of general Formula I are the following:
- methyl 2-carbethoxyamino-2-trimethylsilylacetyleneacetate,
- ethyl 2-carbomethoxyamino-2-triethylsilylacetyleneacetate,
- n-propyl 2-carbo-n-propoxyamino-2-tri-n-propylsilylacetyleneacetate,
- n-butyl 2-carbo-n-butylamino-2-tri-n-butylsilylacetyleneacetate, and
- methyl 2-carbethoxyamino-2-dimethyl-tert-butylsilylacetyleneacetate.

Preferred compounds of general Formula I are those wherein $R_3$ is methyl and each of R and $R_1$ is methyl or ethyl.

The compounds of general Formula I are useful as broad spectrum antibacterial agents being active against both gram positive and gram negative bacteria of the genera, for example, Streptococcus, Escherichia, Staphylococcus, Salmonella, Pseudomonas, Diplococcus, Klebsiella, Proteus, Mycobacterium, Vibrio and Pasteurella and more particularly the species *E. coli, S. schottmuelleri, P. vulgaris, P. mirabilis, P. aeruginosa, S. aureus* and *S. pyogenes*.

As antibacterial agents the compounds of general Formula I can be administered alone or in the form of pharmaceutical preparation either orally, parenterally or topically to warm blooded animals, for example, birds and mammals, such as, cats, dogs, bovine cows, sheep, horses and humans. For oral administration the compounds can be administered in the form of tablets, capsules or pills or in the form of elixirs or suspensions. For parenteral administration the compounds may best be used in the form of a sterile aqueous solution which may contain other solutes, for example, enough saline or glucose to make the solution isotonic. For topical administration the compounds may be formed into creams and ointments by generally known pharmaceutical techniques. The amount of compound of general Formula I administered as an antibacterial agent will vary from about 1 to 250 mg/kg and preferably from about 10 to 50 mg/kg. A typical unit dosage may contain, for example, about 50 mg of a compound of Formula I and may be administered, for example, from 1 to 4 times daily.

The compounds of general Formula I are also useful as starting materials for the preparation of pharmacologically useful compounds of compounds which are intermediates in the preparation of pharmacologically useful agents. The compounds of general Formula I are useful as starting materials for the preparation of compounds of the following general Formula II:

Formula II wherein $R_4$ is hydrogen or a straight chain alkyl group of from 1 to 4 carbon atoms, specifically methyl, ethyl, n-propyl and n-butyl; $R_5$ is hydrogen or $-COOR_7$ wherein $R_7$ is a straight chain alkyl group of from 1 to 4 carbon atoms specifically methyl, ethyl, n-propyl and n-butyl; $R_6$ is hydrogen or $-Si(R_8)_3$ wherein $R_8$ is methyl, ethyl, n-propyl or n-butyl and each $R_8$ is the same, or two of the $R_8$ groups are methyl and the other is tert-butyl; and Z is 3,4-dihydroxybenzyl, 1,3-dioxolan-2-ylethyl, 3-oxopropyl, 3-aminopropyl, 4-aminopropyl, 2-propenyl, 2-carboxyvinyl, carboxyalkyl wherein the alkyl moiety has from 1 to 3 carbon atoms and is straight chained or 5-imidazolymethyl with the proviso that when Z is 3-oxopropyl or 2-propenyl neither of $R_4$, $R_5$ or $R_6$ is hydrogen and when Z is other than 3-oxopropyl or 2-propenyl each of $R_4$, $R_5$ and $R_6$ is hydrogen.

In preparing the compounds of general Formula II 1 equivalent of a glycinate derivative of general Formula I is treated with from 2 to 3 equivalents of a strong base and the thus formed dianion intermediate is alkylated with a reagent selected from 3,4-isopropylidenedioxybenzyl halide wherein the halide is chloride, bromide, iodide or fluoride, 1,3-dioxolan-2-ylethylbromide or iodide, 2-propenal, 3-benzyliminopropyliodide or bromide, 4-benzyliminobutyliodide or bromide, 2-propenylhalide wherein the halide is chloride, bromide or iodide, lower alkyl trans-3-chloro or bromo acrylate, lower alkyl bromo or chloro acetate, lower alkyl acrylate, spiro-(2,5)-5,7-dioxa-6,6-dimethyloct-4,8-dione or 1-tosyl-5-imidazolylmethylbenzoate in a suitable solvent optionally in the presence of a complexing agent such as hexamethylphosphoroustriamide or N,N,N',N'-tetramethylethylenediamine followed by base hydrolysis when Z is other than 3-oxopropyl or 2-propenyl and also acid hydrolysis when Z is other than 1,3-dioxolan-2-ylethyl, 3-oxopropyl or 2-propenyl. Hydrolysis may be achieved by treatment with aqueous base such as sodium hydroxide and aqueous acid such as hydrochloric acid.

When used in reference to the alkylating reagents employed in the above described process and not otherwise defined the term lower alkyl is taken to mean an alkyl group having from 1 to 4 carbon atoms which is straight or branched, for example, methyl, ethyl or isopropyl.

Suitable solvents for the above-described alkylation are aprotic solvents, for example, benzene, toluene, ethers, such as, diethyl ether, tetrahydrofuran, dioxane, dimethylsulfoxide or hexamethylphosphoramide. The alkylation reaction is carried out at about −120° to 25° C, a preferred temperature being −70° C for about ½ hour to 24 hours. The alkylating reagents are known in the art or may be prepared by procedures well known in the art.

Suitable strong bases for the above-described process are, for example, alkyl lithium, such as, butyl lithium, or phenyl lithium, lithium dialkylamide, such as, lithium diisopropylamide, lithium amide, tertiary potassium butylate or sodium amide.

The compound of general Formula II wherein Z is 3,4-dihydroxybenzyl is an irreversible inhibitor of aromatic amino acid decarboxylase rendering said compound useful in the treatment of Parkinsonism when given in conjunction with L-3,4-dihydroxyphenylalanine, depressive syndromes and action myoclonus when administered concurrently with 5-HTP, rheumatoid arthritis and carcinoid syndrome.

The compounds of general Formula II wherein Z is 1,3-dioxolan-2-ylethyl or 3-oxopropyl are useful in the preparation of compounds of the formula

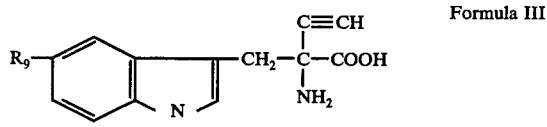

Formula III wherein $R_9$ is hydrogen or hydroxy. The compounds of general Formula III are irreversible inhibitors of aromatic amino acid decarboxylase rendering said compounds useful in the treatment of Parkinsonism when administered concurrently with L-3,4-dihydroxyphenylalanine, depressive syndromes and action myoclonus when administered concurrently with 5-HTP, rheumatoid arthritis and carcinoid syndrome.

The compound of general Formula II wherein Z is 3-aminopropyl is an irreversible inhibitor or ornithine decarboxylase rendering said compound useful as an anti-infective agent and in the control of certain rapid growth processes. This compound is useful, for example, in the treatment of prostatic hypertrophy and psoriasis.

The compound of Formula II wherein Z is 4-aminobutyl is an irreversible inhibitor of lysine decarboxylase rendering said compound useful as an antibacterial agent.

The compound of general Formula II wherein Z is 2-propenyl is useful in the preparation of the following compound

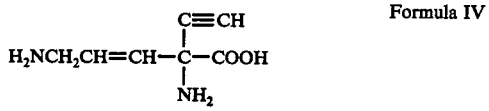

Formula IV which is an irreversible inhibitor of ornithine decarboxylase rendering said compound useful as an anti-infective agent and in the control of certain rapid growth processes. The compound of Formula IV is useful, for example, in the treatment of prostatic hypertrophy and psoriasis.

The compounds of general Formula II wherein Z is carboxyvinyl or carboxyalkyl are irreversible inhibitors of glutamic acid decarboxylase rendering said compounds useful as central nervous system excitatory agents or central nervous system stimulants and antibacterial agents.

The compound of general Formula II wherein Z is 2-imidazolylmethyl is an irreversible inhibitor of histidine decarboxylase rendering said compound useful as an antihistamine agent.

The compounds of general Formula I are prepared by reacting 1 equivalent of a lower alkyl N-carbalkoxy-2-chloro or bromo glycinate of the formula

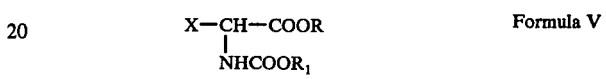

Formula V wherein X is chlorine or bromine and R and $R_1$ have the meanings defined in general Formula I with 1 equivalent of a di-trialkyl acetylene derivative of the formula $(R_3)_3$—Si—C≡C—Si—$(R_3)$ wherein $R_3$ has the meaning defined in general Formula I under the general conditions of a Friedel-Crafts reaction. For example the reaction is carried out in a solvent such as dichloromethane, chloroform, nitrobenzene or carbon disulfide in the presence of 1 equivalent of a strong Lewis acid, for example, aluminum chloride, stannic chloride, borontrihalide wherein halide is chloride, bromide or fluoride or titanium tetrachloride for about 1 to 12 hours at about 0° to 100° C.

The lower alkyl N-carbalkoxy-2-chloro- or bromo glycinate derivatives are obtained by the general procedure of U. Zoller and B. Ben-Ishai, Tetrahedron 31, 863 (1975) only using lower alkyl carbamate wherein the alkyl group has from 1 to 4 carbon atoms and is straight chained for benzyl carbamate. The di-trialkylsilylacetylene compounds are commercially available, known in the art or may be prepared by treating di-metalated acetylene with 2 equivalents of trialkylsilylhalide, that is, bromide or chloride by procedures known in the art.

The following specific examples further illustrate the invention.

Examples 1 to 3 are illustrative of pharmaceutical preparations containing a compound of general Formula I.

EXAMPLE 1

An illustrative composition for hard gelatin capsules is as follows:

| | | |
|---|---|---|
| (a) | methyl 2-carbethoxyamino-2-trimethylsilylacetyleneacetate | 10 mg |
| (b) | talc | 5 mg |
| (c) | lactose | 100 mg |

The formulation is prepared by passing the dry powders of (a) and (b) through a fine mesh screen and mixing them well. The powder is then filled into hard gelatin capsules at a net fill of 115 mg per capsule.

EXAMPLE 2

An illustrative composition for tablet is as follows:

| | | |
|---|---|---|
| (a) | ethyl 2-carbomethoxyamino-2-triethylsilylacetyleneacetate | 5 mg |
| (b) | starch | 43 mg |
| (c) | lactose | 60 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 3

An illustrative composition for an injectable suspension is the following 1 ml ampul for an intramuscular injection.

| | | Weight per cent |
|---|---|---|
| (a) | methyl-2-carbethoxyamino-2-trimethylsilylalacetyleneacetate | 1.0 |
| (b) | polyvinylpyrrolidone | 0.5 |
| (c) | lecithin | 0.25 |
| (d) | water for injection to make | 100.0 |

The materials (a)–(d) are mixed, homogenized, and filled into 1 ml ampuls which are sealed and autoclaved 20 minutes at 121° C. Each ampul contains 10 mg per ml of novel compound (a).

EXAMPLE 4

Methyl 2-trimethylsilylacetylene-2-carbethoxyaminoacetate

To 19.5 g (0.1 M) of methyl N-carbethoxy-2-chloroglycinate and 17.0 g (0.1 M) of bis-trimethylsilyl acetylene in 200 ml of methylene chloride at 0° C is added 13.5 g (0.1 M) of aluminum chloride and the reaction mixture is allowed to warm to 25° C. After 24 hours at 25° C water is carefully added to the mixture which is then extracted with methylene chloride. The combined organic solutions are dried over magnesium sulfate, concentrated and distilled with the b.p. 100°/0.15 mm fraction collected to give methyl 2-trimethylsilylacetylene-2-carbethoxyaminoacetate.

When in the procedure of Example 4 an appropriate amount of ethyl N-carbomethoxy-2-chloroglycinate or methyl N-carbopropoxy-2-chloroglycinate is substituted for methyl N-carbethoxy-2-chloroglycinate and an appropriate amount of bis-triethylsilyl acetylene or di-dimethyl-tert-butylsilylacetylene is substituted concurrently for bis-trimethylsilyl acetylene the following respective compounds are obtained: ethyl 2-triethylsilylacetylene-2-carbomethoxyaminoacetate and methyl 2-dimethyl-tert-butylsilylacetylene-2-carbopropoxyamino acetate.

The following examples illustrate the use of compounds of general Formula I in the preparation of compounds of general Formula II.

EXAMPLE 5

2-Acetylene-2-amino-3-(3,4-dihydroxyphenyl)propionic Acid

A solution of 2.57 g (10 mM) of methyl 2-trimethyl silylacetylene-2-carbethoxyaminoacetate in 5 ml of tetrahydrofuran is added to lithium diisopropylamide, prepared from 3.02 g (30 mM) of diisopropylamine and 15 ml of a 2 M solution of n-butyllithium, in 70 ml of tetrahydrofuran containing 5 ml of hexamethylphosphortriamide at −78° C. After 5 minutes at −78° C 2.43 g (10 mM) of 3,4-isopropylidenedioxybenzylbromide in 5 ml of tetrahydrofuran is added. The solution is maintained at −78° C for 4 hours after which 1.1 g (20 mM) of acetic acid is added then the mixture is poured into water and extracted with ether. The ether solution is washed well with water, dried and concentrated leaving a residue which is purified by chromatography on Florisil to give methyl 2-carbethoxyamino-3-(3,4-isopropylidenedioxyphenyl)-2-trimethylsilylpropionate which is suspended in 50 ml of 6 N HCl and heated under reflux for 4 hours after which the solvent is evaporated. The resulting residue is dissolved in the minimum quantity of water and the pH adjusted to 5 by the addition of hydrazine. The solution is cooled to 0° C and the resulting precipitate collected to give 2-acetylene-2-amino-3-(3,4-dihydroxyphenyl)propionic acid.

EXAMPLE 6

Methyl 2-carbethoxy-2-trimethylsilylacetylene-2-(1,3-dioxolan-2-yl)butyrate

When in the procedure of Example 5 1.81 g (10 mM) of 1,3-dioxolan-2-ylethylbromide is substituted for 3,4-isopropylidenedioxybenzylbromide, methyl 2-carbethoxy-2-trimethylsilylacetylene-4-(1,3-dioxolan-2-yl)butyrate is obtained which may be used to prepare the compound of Formula III as follows. To 1.22 g (0.005 M) of p-benzyloxyphenylhydrazine HCl in 200 ml of ethanol and 28 ml of 5% HCl is added slowly 1.8 g (0.005 M) of the butyrate dissolved in 5 ml of ethanol. The mixture is maintained at 90° C for 4 hours then evaporated to dryness. The resulting residue is dissolved in the minimum quantity of methanol and allowed to crystallize to afford methyl 2-trimethylsilyl-2-ethoxycarbonylamino-3-[3-(5-benzyloxy)indolyl]propionate. A solution of 0.99 g (0.002 M) of the indole propionate in 20 ml of dichloromethane at −70° C is treated with 125 mg (0.005 M) of boron tribromide. The mixture is allowed to warm to about 25° C then 10 ml of methanol is added and the solvent evaporated. The residue is treated with 50 ml of 3 N HCl at reflux for 12 hours then evaporated.

The resulting residue is taken up in the minimum quantity of water, the pH adjusted to 6 and applied to an Amberlite resin 120 H+. Elution with 1 M ammonium hydroxide affords 2-acetylene-2amino-3-[3-(5-hydroxy)indolyl]propionic acid which is recrystallized from water-ethanol.

EXAMPLE 7

Methyl 2-carbethoxyamino-5-oxo-2-trimethylsilylacetylenepentanoate

A solution of 1.28 g (5 mM) of methyl 2-carbethoxyamino-2-trimethylsilylacetyleneacetate in 20 ml of tetrahydrofuran is added to a solution of lithium diisopropylamide, prepared from 1.5 g (15 mM) of diisopropylamine and 7.5 ml of a 2 M solution of n-butyllithium, in 60 ml of tetrahydrofuran containing 10 ml of hexamethylphosphortriamide at −78° C. After 10 minutes at −78° C 280 mg (5 mM) of 2-propenal is added followed by the addition of 600 mg of acetic acid. The solution is diluted with ether and washed with water. The ether solution is dried and concentrated to afford the methyl 2-carbethoxyamino-5oxo-2-trimethylsilylacetylenepentanoate which can be used to prepare a compound of Formula III as follows.

To 1.23 g (0.005 M) of p-benzyloxyphenylhydrazine hydrochloride in 200 ml of ethanol and 28 ml of 5% HCl is added slowly 1.5 g (5 mM) of methyl 2-carbethoxyamino-5-oxo-2-trimethylsilylacetylenepentanoate dissolved in 5 ml of ethanol. The mixture is maintained at 90° C for 2 hours then evaporated to dryness. The residue is dissolved in the minimum quantity of hot methanol and allowed to crystallize to afford methyl 2-trimethylsilylacetylene-2-carbethoxyamino-3-[3-(5-benzyloxy)indolyl]propionate 0.99 g (0.002 M) of which in 20 ml of dichloromethane at −70 ° C is treated with 125 mg (0.005 M) of boron trichloride. The mixture is allowed to warm to about 25° C then 10 ml of methanol is added and the solvent evaporated. The resulting residue is treated with 50 ml of 3 N HCl at reflux for 12 hours then evaporated leaving a residue which is taken up in the minimun quantity of water, the pH adjusted to 6 and applied to an Amberlite resin 120 H+. Elution with 1 M ammonium hydroxide affords 2-acetylene-2-amino-3-[3-(5-hydroxy)indolyl]propionic acid which is recrystallized from ethanol.

EXAMPLE 8

2-Acetylene-2-amino-3-(5-imidazolyl)propionic Acid Dihydrochloride

A solution of 1.28 g (5 mM) of methyl 2-carbethoxyamino-2-trimethylsilylacetylenacetate is added to a solution of lithium diisopropylamide, prepared from 1.51 g (15 mM) of diisopropylamine and 7.5 ml of a 2M solution of n-butyllithium, in 60 ml of tetrahydrofuran containing 8 ml of hexamethylphosphortriamide at −78° C. After 10 minutes at −78° C 1.7 g (5 mM) of 1-tosyl-5-imidazolylmethyl benzoate in 10 ml of tetrahydrofuran is added. After 3 hours at −30° C 300 mg of acetic acid is added and the mixture diluted with ether. The ether solution is washed with brine, dried and concentrated leaving a residue which is recrystallized from methanol then heated in 20 ml of 6 N HCl overnight. On cooling the solution is washed with ether and concentrated leaving a resuide which is recrystallized from isopropyl alcohol to give 2-acetylene-2-amino-3-(5-imidazolyl)propionic acid dihydrochloride.

The 1-tosyl-5-imidazolylmethyl benzoate employed in the above procedure is prepared by adding to a solution of 2.5 g (10 mM) of 1-tosyl-4-hydroxymethylimidazole in 10 ml of chloroform 2.0 g (20 mM) of triethylamine followed by the addition of 1.4 g (10 mM) of benzoylchloride. After 5 hours the solution is washed with water, aqueous sodium bicarbonate, dried and concentrated leaving a residue which is recrystallized from ethyl acetate to give 1-tosyl-5-imidazolylmethyl benzoate.

EXAMPLE 9

2-Acetylene-2,5-diaminopentanoic Acid Monohydrochloride

A solution of methyl 2-carbethoxy-2-trimethylsilylacetyleneacetate (2.5 g, 10 mM) in 20 ml of tetrahydrofuran is added to a solution of lithium diisopropylamide, prepared from 3.03 q (30 mM) of diisopropylamine and 15 ml of a 2 M solution of n-butyllithium, in 60 ml of tetrahydrofuran containing 10 ml of hexamethylphosphortriamide at −78° C. After 15 minutes at −78° C 2.2 g (10 mM) of 3-benzyliminopropyliodide in 10 ml of tetrahydrofuran is added. The mixture is maintained at −70° C for 3 hours then 1.2 g (20 mM) of acetic acid is added followed by water. The mixture is extracted with ether and the ether solution dried and concentrated leaving a resudue which is treated with 50 ml of 3 N HCl for 12 hours at reflux. On cooling the solution is washed with dichloromethane then concentrated to dryness. The resulting residue is dissolved in the minimum quantity of ethanol then 1.01 g (10 mM) of triethylamine is added. The resulting precipitate is collected and recrystallized from water-ethanol to give 2-acetylene-2,5-diaminopentanoic acid monohydrochloride.

The 3-benzyliminopropyliodide used in the above procedure is obtained from the corresponding bromide derivative by treatment with sodium amide.

When in the procedure of Example 9 an appropriate amount of 2-propenylbromide is substituted for 3-benzyliminopropyliodide and the reaction stopped just prior to the hydrolysis step with 3 N HCl, methyl 2-carbethoxyamino-2-trimethylsilylacetylenepent-4-enoate is obtained which may be used to prepare the compound of general Formula IV as follows. A solution of 2.97 g (10 mM) of the pent-4-enoate in 20 ml of ethanol and 5 ml of water is treated with 1.11 g (10 mM) of selenium dioxide and the mixture heated at reflux for 4 hours. The solvent is then evaporated, the residue taken up in either and washed with sodium bicarbonate solution. The ether solution is dried, evaporated and the diaster iomeric mixture of allylic alcohols purfied by chromatography on Florisil. A solution of 3.1 g (10 mM) of the alcohol in 20 ml of tetrahydrofuran is added to 24 mg of a 50% dispension of sodium hydride. After 5 minutes at about 25° C this solution is added dropwise via syringe to a solution of 1.44 g (10 mM) of trichloroacetonitrile in 110 ml of tetrahydrofuran precooled to −23° C. The resulting solution is stirred for 1½ hours at −23° C then evaporated at room temperature leaving an oil which is dissolved in 40 ml of xylene and heated at reflux for 3 hours then allowed to stand overnight at room temperature. The resulting precipitate is collected and recrystallized from chloroform to give the trichloromethyl acetamide 1 g (2.1 mM) of which in 30 ml of methanol and 30 ml of 6 N HCl is heated at reflux for 12 hours then concentrated. The residue is washed well with chloroform, treated with charcoal, filtered and evaporated leaving a residue which is recrystallized from water-ethanol to give 2-acetylene-2,5-diaminopent-3-enoic acid dihydrochloride.

We claim:

1. A compound of the Formula

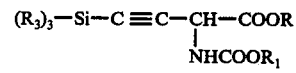

wherein each of R and $R_1$ is methyl, ethyl, n-propyl or n-butyl and may be the same or different and $R_3$ is methyl, ethyl, n-propyl or n-butyl and each $R_3$ is the same or two $R_3$ groups are methyl and the other $R_3$ group is tert-butyl.

2. A compound of claim 1 wherein each of R and $R_1$ is methyl or ethyl.

3. A compound of claim 1 wherein each $R_3$ group is methyl.

* * * * *

UNITED STATES PATENT AND TRADEMARK OFFICE
CERTIFICATE OF CORRECTION

PATENT NO. : 4,088,667

DATED : May 9, 1978

INVENTOR(S) : P.J. Casara, M. Jung and B.W. Metcalf

It is certified that error appears in the above-identified patent and that said Letters Patent are hereby corrected as shown below:

Column 2, line 18 ...of... should read "or". Column 3, line 43 ... -dihyroxy- ... should read "-dihydroxy-". Column 6, line 68 ... -5oxo- ... should read "-5-oxo-". Column 7, line 63 ...3.03 q... should read "3.03 g". Column 8, line 5, ...resudue... should read "residue"; line 28 ...either... should read "ether"; line 30 ...purfied... should read "purified".

Signed and Sealed this

Second Day of January 1979

[SEAL]

Attest:

RUTH C. MASON
Attesting Officer

DONALD W. BANNER
Commissioner of Patents and Trademarks